(12) United States Patent
Zhang et al.

(10) Patent No.: US 10,041,106 B2
(45) Date of Patent: Aug. 7, 2018

(54) METHODS AND COMPOSITIONS FOR ISOTHERMAL WHOLE GENOME AMPLIFICATION

(75) Inventors: Haichuan Zhang, San Diego, CA (US); Zuxu Yao, San Diego, CA (US); Kerry Gunning, San Diego, CA (US)

(73) Assignee: Progenity, Inc., San Diego, CA (US)

(*) Notice: Subject to any disclaimer, the term of this patent is extended or adjusted under 35 U.S.C. 154(b) by 938 days.

(21) Appl. No.: 14/115,619

(22) PCT Filed: May 4, 2012

(86) PCT No.: PCT/US2012/036671
§ 371 (c)(1),
(2), (4) Date: May 16, 2014

(87) PCT Pub. No.: WO2012/154614
PCT Pub. Date: Nov. 15, 2012

(65) Prior Publication Data
US 2014/0295419 A1    Oct. 2, 2014

Related U.S. Application Data

(60) Provisional application No. 61/483,636, filed on May 6, 2011.

(51) Int. Cl.
| | | |
|---|---|---|
| C12Q 1/68 | (2018.01) | |
| C12Q 1/6806 | (2018.01) | |
| C12Q 1/6865 | (2018.01) | |

(52) U.S. Cl.
CPC ......... *C12Q 1/6806* (2013.01); *C12Q 1/6865* (2013.01); *C12Q 2525/197* (2013.01)

(58) Field of Classification Search
None
See application file for complete search history.

(56) References Cited

U.S. PATENT DOCUMENTS

| | | | | |
|---|---|---|---|---|
| 5,501,963 A | * | 3/1996 | Burckhardt | C12Q 1/686 |
| | | | | 435/267 |
| 2008/0220422 A1 | * | 9/2008 | Shoemaker | C12Q 1/6809 |
| | | | | 435/6.12 |
| 2008/0261275 A1 | | 10/2008 | Liss | |
| 2010/0129874 A1 | * | 5/2010 | Mitra | C12Q 1/686 |
| | | | | 435/91.2 |
| 2011/0033854 A1 | * | 2/2011 | Drmanac | C12P 19/34 |
| | | | | 435/6.12 |

FOREIGN PATENT DOCUMENTS

| | | | |
|---|---|---|---|
| WO | WO 2005/047532 A1 | 5/2005 | |
| WO | WO 2009/105531 A1 | 8/2009 | |
| WO | WO 2010075459 A1 * | 7/2010 | ........... C12Q 1/6806 |

OTHER PUBLICATIONS

Zhang et al. Proceedings of the National Academy of Sciences, USA 1992; 89: 5847-5851.*
Sendler et al. Nucleic Acids Research 2013; 41: 4104-4117.*
Ren et al. Molecular Human Reproduction 2007; 13: 431-436.*
Hosono et al. Genome Research 2003; 13: 954-964.*
Feuchtenberger M et al., "Semiquantitative and qualitative assessment of B-lymphocyte $V_H$ repertoire by a fluorescent multiplex PCR", Journal of Immunological Methods 276 (2003) 121-127.
A.H. Handyside, "Isothermal whole genome amplification from single and small Numbers of cells: a new era for preimplantation genetic diagnosis of inherited disease", Molecular Human Reproduction vol. 10, No. 10, pp. 767-772, 2004.
Guangqiu Li et al., "CD133* single cell-derived progenies of colorectal cancer cell line SW480 with different invasive and metastatc potential", Clin Exp. Metastasis (2010), 27: 517-527.
Sciortino et al., "Involvement of gD/HVEM interaction in NF-κB-dependent inhibition of apoptosis by HSV-1 gD", Biochemical Pharmacology 76 (2008) 1522-1532.
Fabian et al., "TRPC1 channels regulate directionality of migrating cells", Pfluger Arch—Eur. J. Physiol (2008) 457: 475-484.
Strijbosch et al., "Limiting dilution assays", Journal of Immunological Methods, vol. 97, No. 1, Feb. 26, 1987, pp. 133-140.
Zhou et al., "Closed-tube genotyping with unlabeled oligonucleotide probes and a saturating DNA dye" Clinical Chemistry, 2004. vol. 50, No. 8, pp. 1328-1335.

* cited by examiner

*Primary Examiner* — Angela M. Bertagna
(74) *Attorney, Agent, or Firm* — Knobbe, Martens, Olson & Bear, LLP

(57) ABSTRACT

Disclosed are methods and compositions for amplification of genetic material, including isothermal WGA of single cells.

23 Claims, 6 Drawing Sheets

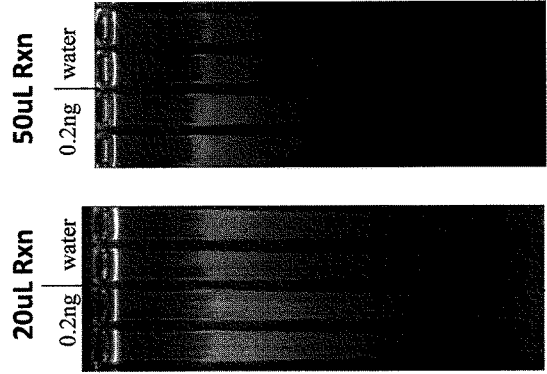
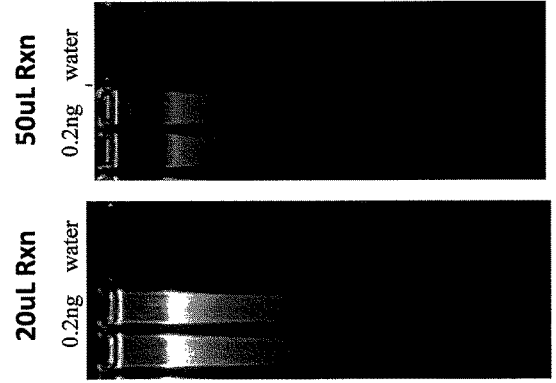
FIG. 1A
FIG. 1B

| plate # | Target cell (male) | RBCs (female) | Target: RBC ratio | XY PCR analysis ||||| | | SRY2 ||| X2 |||
|---|---|---|---|---|---|---|---|---|---|---|---|---|---|---|---|
| | | | | total WGA rxns | positive WGA rxns | no WGA product | % WGA | both SRY2 and X2 | X2 only (SRY2 DO) | SRY2 only (X2 DO) | SRY2 DO% | X2 DO% | mean Ct. (WGA) | Ct. stdev | mean Ct. (WGA) | Ct. stdev |
| 1 | 1 | 0 | 1:0 | 72 | 58 | 14 | 80.6% | 36 | 8 | 14 | 13.8% | 24.1% | 28.0 | 2.7 | 26.7 | 6.9 |
| | 1 | 500 | 1:500 | 72 | 49 | 23 | 68.1% | 35 | 4 | 10 | 8.2% | 20.4% | 27.9 | 3.3 | 26.5 | 3.0 |
| | 1 | 2500 | 1:2500 | 72 | 58 | 14 | 80.6% | 43 | 3 | 12 | 5.2% | 20.7% | 27.2 | 2.3 | 26.1 | 2.4 |
| | 1 | 5000 | 1:5000 | 72 | 60 | 12 | 83.3% | 48 | 0 | 12 | 0.0% | 20.0% | 27.5 | 2.3 | 26.7 | 2.2 |
| | 1 | 50,000 | 1:50,000 | 72 | 57 | 15 | 79.2% | 43 | 4 | 10 | 7.0% | 17.5% | 27.3 | 2.3 | 26.7 | 2.0 |
| 2 | 1 | 0 | 1:0 | 72 | 56 | 16 | 77.8% | 31 | 5 | 20 | 8.9% | 35.7% | 28.1 | 2.9 | 27.0 | 6.7 |
| | 1 | 500 | 1:500 | 72 | 56 | 16 | 77.8% | 35 | 7 | 14 | 12.5% | 25.0% | 27.4 | 2.5 | 26.6 | 2.9 |
| | 1 | 2500 | 1:2500 | 72 | 59 | 13 | 81.9% | 46 | 4 | 9 | 6.8% | 15.3% | 28.4 | 3.4 | 26.3 | 2.3 |
| | 1 | 5000 | 1:5000 | 72 | 58 | 14 | 80.6% | 48 | 4 | 6 | 6.9% | 10.3% | 27.6 | 2.9 | 26.3 | 2.3 |
| | 1 | 50,000 | 1:50,000 | 72 | 56 | 16 | 77.8% | 45 | 1 | 10 | 1.8% | 17.9% | 27.7 | 2.7 | 26.9 | 2.5 |

FIG. 5

|  | Plate 1 | | | | Plate 2 | | | |
| --- | --- | --- | --- | --- | --- | --- | --- | --- |
| Target cell:RBC ratio | 1:0 | 1:5000 | 1:50000 | | 1:0 | 1:5000 | 1:50000 | |
| total WGA | 24 | 24 | 24 | | 24 | 24 | 21.56 | |
| total loci | 432 | 432 | 432 | | 432 | 432 | 388 | |
| Heterozygous | 246 | 331 | 343 | | 229 | 302 | 318 | |
| Homozygous (ADO) | 177 | 96 | 88 | | 183 | 128 | 112 | |
| ND (LDO) | 9 | 5 | 1 | | 20 | 2 | 2 | |
| Heterozygous | 56.9% | 76.6% | 79.4% | | 53.0% | 69.9% | 73.6% | |
| Homozygous (ADO) | 41.0% | 22.2% | 20.4% | | 42.4% | 29.6% | 25.9% | |
| ND (LDO) | 2.1% | 1.2% | 0.2% | | 4.6% | 0.5% | 0.5% | |

FIG. 6

METHODS AND COMPOSITIONS FOR ISOTHERMAL WHOLE GENOME AMPLIFICATION

RELATED APPLICATIONS

This application claims priority to U.S. Provisional Patent Application Ser. No. 61/483,636, filed on May 6, 2011, which is hereby incorporated by reference herein in its entirety.

BACKGROUND OF THE INVENTION

Field of the Invention

The present invention is in the field of methods and compositions for amplification, including methods and compositions for isothermal whole genome amplification (WGA) of single cells.

Description of the Related Art

Standard isothermal WGA protocols instruct technicians to use at least 10 ng (or 1,500 cell equivalents) of starting genomic material to carry out a successful isothermal WGA reaction. Groups have tried and failed to perform single cell isothermal WGA. For example, standard procedures for isothermal WGA on single cell genomic material have resulted in undesirable outcomes, such as high allele dropout (ADO) and locus dropout (LDO) rates, with some reports of >30% for ADO using ≥10 ng of starting genomic material (Morrison et al., *Am J Trop Med Hyg.* 76 (2007) 1132-1137). Standard procedures have also demonstrated amplification bias and "noise" in array comparative genomic hybridization (array CGH) output. Further, standard cell lysis conditions performed prior to WGA often result in damage (e.g., nicking, breaking, and/or fragmenting) of the genetic material, which can compromise the performance of subsequent methods such as WGA and array CGH (Kumar et al., *Biotechniques* 44 (2008) 879-890). Because of these problems, the preferred method for WGA from a single cell has been a non-isothermal, or PCR-based, method.

Further, isolating genomic DNA from whole blood requires extensive purification. Standard protocols, such as that provided with the GENOMIPHI™ DNA Amplification Kit (GE Healthcare, Waukesha, Wis.), indicate that blood components such a heme can inhibit Phi29 DNA polymerase. Studies in which these protocols have been used demonstrate that Phi29 is strongly inhibited by high concentrations of heme, with samples derived from blood producing negative results following WGA (Ballantyne et al., Forensic Science International 166 (2007) 35-41). Because of this problem, standard WGA protocols involve purification steps to eliminate red blood cells in order to prevent decreased yields and background amplification.

Thus, there is a need for improved methods and compositions for preparing samples for isothermal WGA and array CGH (particularly methods and compositions for preparing low levels of genomic material, such as genomic material from a single cell), methods and compositions for generating consistent amplified products with low bias, and methods and compositions that can be scaled up for high throughput performance and analyses.

SUMMARY OF THE INVENTION

Embodiments of the present invention relate to methods and compositions for amplification of genetic material from cells. In preferred embodiments, whole genome amplification is performed for low levels of genomic material, such as a single cell.

One embodiment of the invention is a method of preparing DNA from a cell for amplification, comprising: preparing a lysis mixture of: a sample comprising a cell containing DNA; oligonucleotides; and a lysis buffer solution; and incubating the mixture for up to 30 minutes, thereby lysing the cell in the mixture.

Another embodiment of the invention is a method of preparing DNA from a cell for a high throughput whole genome amplification, comprising: obtaining a sample comprising cells containing DNA; aliquoting at least 300 subsamples of the sample, where the subsamples each contain an average of less than about one cell containing DNA; adding to each subsample: oligonucleotides; and a lysis buffer solution; incubating the subsamples containing the oligonucleotides and lysis buffer solution for up to 30 minutes, thereby lysing the cells; adding a neutralization solution and an amount of oligonucleotide primers sufficient for amplification of the DNA to the lysed subsamples; heating the neutralized subsamples for less than 2 minutes to denature DNA in the neutralized subsamples; and cooling the neutralized subsamples.

Another embodiment of the invention is a method of amplifying genetic material, comprising: preparing a mixture comprising: genetic material from up to 100 cells; oligonucleotide primers; a polymerase; dNTPs; a salt mixture; and incubating the mixture to permit an amplification reaction, where the incubation does not include a heat denaturation step.

Another embodiment of the invention is a method of performing an array comparative genomic hybridization (array CGH), comprising: obtaining the product from a genetic amplification of a single cell according to a method described herein; and performing array CGH on the product.

Another embodiment of the invention is a method of identifying a genetic variation, comprising: obtaining the product from a genetic amplification of a single cell according to a method described herein; performing a sequencing reaction on the product; and analyzing the sequenced product to identify a genetic variation. In some embodiments, more than one cell is used in the methods of the present invention.

Another embodiment of the invention is a solution comprising: a biological solution containing a single nucleated cell; an added base; and an added reducing agent.

Another embodiment of the invention is a composition for isothermal whole genome amplification, comprising: a base; a reducing agent; and a chelator.

Another embodiment of the invention is a composition for isothermal whole genome amplification comprising: a base; and a chelator.

Another embodiment of the invention is a composition for isothermal whole genome amplification, comprising: a solution comprising a biological solution containing a single nucleated cell; an added base; and an added reducing agent; oligonucleotide primers; a DNA polymerase; dNTPs; and a composition comprising a base; a reducing agent; and a chelator.

Another embodiment of the invention is a composition for isothermal whole genome amplification, comprising: a solution comprising a biological solution containing a single nucleated cell; an added base; and an added reducing agent; oligonucleotide primers; a DNA polymerase; dNTPs; and a composition comprising a base and a chelator.

Another embodiment of the invention is a composition for decreasing template-independent polymerization in a whole genome amplification, comprising: oligonucleotide primers, where at least a portion of the oligonucleotide primers comprises a C3 spacer; a polymerase; dNTPs; and a salt mixture.

Some embodiments of the invention comprise a method further comprising adding a neutralization solution to the mixture following incubation; heating the neutralized mixture for less than 2 minutes to denature DNA in the neutralized mixture; and cooling the neutralized mixture.

Some embodiments of the invention comprise the following: a method where the concentration of the oligonucleotides in the mixture is between 10 uM and 100 uM; a method where the lysis buffer solution comprises a base and a reducing agent; a method where the lysis buffer solution does not comprise a chelator; a method where the incubation of the lysis mixture is at 20° C. to 35° C.; a method where the incubation of the lysis mixture is for up to 3 minutes; a method where the neutralization solution comprises a phosphate salt and a chelator; a method where the chelator is a divalent ion chelator; a method where heating the neutralized mixture comprises heating the mixture at 80° C. to 95° C. for less than two minutes; a method where the total volume of the neutralized mixture is less than 4 uL; a method where the total volume of the neutralized mixture is less than or about 1 uL; a method that does not include vortexing; a method where the oligonucleotides are oligonucleotide primers; a method where the oligonucleotide primers are random oligonucleotide primers; a method further comprising adding oligonucleotide primers to the mixture following the incubation of the lysis mixture; a method where the oligonucleotides and the oligonucleotide primers are different; a method where the oligonucleotides and the oligonucleotide primers are the same; a method where the concentration of the additional oligonucleotide primers added to the lysed mixture is between 100 uM and 400 uM; a method where the oligonucleotide primers are random oligonucleotide primers; a method where the amount of oligonucleotide primers is at least 100 uM; a method further comprising performing whole genome amplification on a neutralized subsample; a method where the reaction volume of the lysed subsample is less than 30% of the reaction volume in which the whole genome amplification is performed; a method where the genetic material is from a single cell; a method where the genetic material is at least one chromosome per cell; a method where the genetic material is obtained from cells from a biological sample comprising a mixture of maternal and fetal cells; a method where the polymerase is a thermostable polymerase; a method where the polymerase has strand displacement activity; a method where the salt mixture comprises: Tris-HCl; NaCl or KCl; $MgCl_2$ or $MnCl_2$; and $(NH_4)_2SO_4$; a method where the mixture further comprises red blood cells in a concentration of at least 500 cells/ul; a method where the mixture further comprises a lysis buffer solution and a neutralization solution; a method where the lysis buffer solution comprises a base and a reducing agent; a method where the lysis buffer solution consists essentially of a base and a reducing agent; a method where the neutralization solution comprises a phosphate salt and a chelator; a method where the genetic material is prepared according to a method described herein; a method where the oligonucleotide primers are random oligonucleotides; a method where at least a portion of the oligonucleotides or oligonucleotide primers are $SpC_3$—$N_9$ primers, where N is any nucleotide, and where $SpC_3$ is a three carbon molecule; a method where at least a portion of the oligonucleotides or oligonucleotide primers are N-$SpC_3$—$N_9$ primers, where N is any nucleotide, and where $SpC_3$ is a three carbon molecule; a method where at least a portion of the oligonucleotide primers comprise a modified-base pairing combination; a method where the modified-base pairing combination is 2,6-diaminopurine and 5-(1-propynyl)-2'-deoxy-Uridine (DAP/pdU); a method where the mixture further comprises at least one selected from the group consisting of BSA, IPP, and TIPP; a method where the mixture further comprises BSA; a method where the total volume of the mixture is less than 4 uL; a method where the total volume of the mixture is less than 1 uL; a method where the incubation of the mixture is between 4° C. and 50° C.; a method where the amplification reaction is an incubation of the mixture under isothermal conditions for at least 30 minutes; a method further comprising heating the mixture to inactivate the polymerase after the incubation for amplification; a method further comprising performing analysis of locus dropout (LDO) rates; a method further comprising performing analysis of allele dropout (ADO) rates; a method where, other than lysis of a cell, DNA extraction has not been performed on the genetic material; a method where lysis has been performed, and where the genetic amplification is performed in the location in which the lysis was performed; a method where the location is a microwell on a plate; a method further comprising dividing the product of the genetic amplification into at least two aliquots; a method further comprising performing a test on at least one of the aliquots to identify a fetal cell; a method further comprising performing a test on at least one of the aliquots to identify a genetic variation; a method further comprising performing a second genetic amplification on at least one of the aliquots; a method further comprising dividing the product of the second genetic amplification into at least two subsamples; a method further comprising performing a test on at least one of the subsamples from the second genetic amplification to identify a fetal cell; a method further comprising performing a test on at least one of the subsamples from the second genetic amplification to identify a genetic variation; a method further comprising: pooling subsamples identified as containing a fetal allele; and performing a test on the pooled subsamples to identify a genetic variation; a method further comprising pooling a remaining aliquot from at least two cells identified as containing a fetal allele; and performing a second genetic amplification on the pooled aliquots; a method further comprising pooling the product of the genetic amplification or a portion thereof, with the product of another genetic amplification or portion thereof; and performing a second genetic amplification on the pooled products; a method where less than 50% of the product from one or both of the genetic amplifications is used to perform the second genetic amplification; a method where the genetic material from a single cell is obtained from a sample generated in a first genetic amplification; a method further comprising obtaining the product from a genetic amplification of a single cell according to a method described herein; and performing array CGH on the product; a method further comprising obtaining the product from a genetic amplification of a single cell according to a method described herein and performing a sequencing reaction on the product; a method further comprising pooling the products of at least five genetic amplifications of single cells prior to performing the array CGH; a method where the array CGH is performed to identify a genetic variation; and a method where the genetic variation is a copy number variation (CNV).

Some embodiments of the invention comprise a method where the salt mixture comprises: Tris-HCl; NaCl or KCl; $MgCl_2$ or $MnCl_2$; and $(NH_4)_2SO_4$.

Some embodiments of the invention comprise a method further comprising: pooling subsamples identified as containing a fetal allele; and performing a test on the pooled subsamples to identify a genetic variation.

Some embodiments of the invention comprise a method further comprising: pooling a remaining aliquot from at least two cells identified as containing a fetal allele; and performing a second genetic amplification on the pooled aliquots.

Some embodiments of the invention comprise a method further comprising: pooling the product of the genetic amplification or a portion thereof, with the product of another genetic amplification or portion thereof; and performing a second genetic amplification on the pooled products.

Some embodiments of the invention comprise the following: a biological fluid further comprising random oligonucleotides.

Some embodiments of the invention comprise a composition further comprising: oligonucleotide primers; a DNA polymerase; dNTPs; a base; a reducing agent; and a chelator.

Some embodiments of the invention comprise a composition further comprising: oligonucleotide primers; a DNA polymerase; dNTPs; a base; and a chelator, Some embodiments of the invention comprise the following: a solution comprising not more than one nucleated cell; a composition comprising not more than one nucleated cell; a solution comprising only one nucleated cell; a composition comprising only one nucleated cell; a solution consisting of not more than one nucleated cell; a composition consisting of not more than one nucleated cell; a solution consisting of only one nucleated cell; a composition consisting of only one nucleated cell; a composition where at least a portion of the oligonucleotide primers are $SpC_3$—$N_9$ primers, where N is any nucleotide, and where $SpC_3$ is a three carbon molecule; a composition where at least a portion of the oligonucleotide primers are N-$SpC_3$—$N_9$ primers, where N is any nucleotide, and where $SpC_3$ is a three carbon molecule; a composition where at least a portion of the oligonucleotide primers comprise a modified-base pairing combination; and a composition where the modified-base pairing combination is 2,6-diaminopurine and 5-(1-propynyl)-2'-deoxy-Uridine (DAP/pdU), Some embodiments of the invention comprise a composition where the salt mixture comprises: Tris-HCl; NaCl or KCl; $MgCl_2$ or $MnCl_2$; and $(NH_4)_2SO_4$.

BRIEF DESCRIPTION OF THE DRAWINGS

FIGS. 1A and 1B set forth data from methods and compositions of embodiments of the present invention showing decreased template-independent polymerization in whole genome amplification.

FIGS. 4A and 4B set forth data from methods and compositions of embodiments of the present invention showing reduced genomic damage and improved whole genome amplification.

FIG. 5 sets forth data from methods and compositions of embodiments of the present invention showing improved quality of whole genome amplified genomic material from target cells in the presence of red blood cells.

FIG. 6 sets forth data from methods and compositions of embodiments of the present invention showing improved quality of whole genome amplified genomic material from target cells in the presence of red blood cells.

DETAILED DESCRIPTION OF THE PREFERRED EMBODIMENT

Figure 2B:
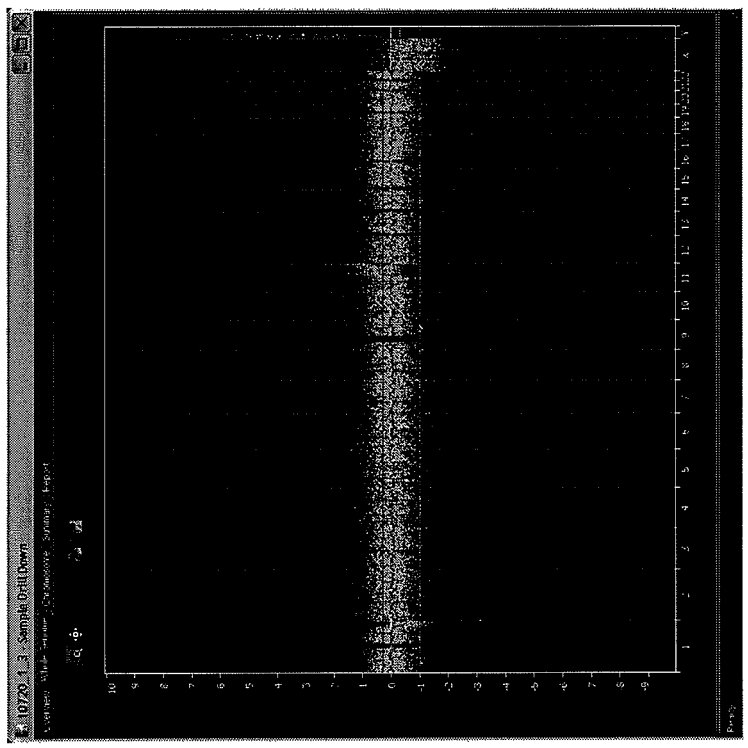
FIGS. 2A and 2B set forth data from methods and compositions of embodiments of the present invention showing improved whole genome amplified genomic material by array comparative genomic hybridization.

Embodiments of the present invention relate to methods and compositions for whole genome amplification, including methods and compositions for isothermal whole genome amplification of single cells. The methods and compositions described herein generate an unexpectedly high quality of amplification products, as evidenced by reduced locus and allele dropout (LDO and ADO) rates, improved sequencing and array CGH data using amplification products, or target identification in amplification products. Further, the methods and compositions described herein can generate a high quality and substantial quantity of amplification products in a short period of time from a little as a single target cell. The products generated using the methods and compositions described herein are useful for any DNA-based diagnostic application, including but not limited to PCR genotyping, array CGH analysis of copy number variation (CNV), and DNA sequencing analysis. By utilizing the methods and compositions described herein, particularly on a cell-by-cell basis, embodiments of the invention overcome problems presented by current protocols for amplification, including problems presented for WGA.

Several of the methods and compositions described herein can be used to improve the performance and/or efficiency of amplification reactions. For example, cell lysis and amplification can be performed on a sample without an intervening DNA extraction step, oligonucleotides can be added to a cell lysis solution to prevent DNA from adhering to its physical surroundings in order to reduce loss of DNA, and WGA reactions can include reagents such as bovine serum albumin (BSA) or inorganic pyrophosphatases (IPPs). Further, methods can include optimized cell lysis buffers, minimization of mechanical manipulation, brief heat denaturation, and high oligonucleotide primer concentrations in order to maintain the integrity of genomic DNA prior to or during an amplification reaction.

Several of the methods and compositions described herein can be used to generate consistent products with low amplification bias. For example, following amplification, samples can be pooled prior to analysis of single cell amplification products. Consistency and quality of products can be measured, for example, by assessing WGA, sequencing or array CGH data for the products generated as described herein.

Several of the methods and compositions described herein enable WGA to be performed in low volume reactions, making WGA particularly cost effective and high throughput. In some embodiments, the same oligonucleotide is used for cell lysis and WGA reactions. In some embodiments, fully automated systems are used to carry out the methods described herein.

In some embodiments, the methods and compositions described herein are used to isolate, amplify, detect, and/or test fetal cells from a mixture of maternal and fetal cells. Methods of enriching, detecting, and testing fetal alleles are described in U.S. patent application Ser. No. 12/645,129, which is incorporated herein by reference in its entirety. In some embodiments, the methods and compositions described herein are used to amplify, detect, and/or test fetal cells from embryos. For example, in some embodiments, the methods and compositions described herein are used in conjunction with pre-implantation genetic diagnosis (PGD).

In specific embodiments, a maternal sample is split into subsamples such that each subsample contains an average of only one cell. In a more preferred embodiment, a maternal sample is split into subsamples such that each subsample contains an average of less than one cell. The subsamples are individually combined with oligonucleotides and an alkaline lysis buffer to release genomes from the cells with minimal mechanical manipulation. Without further DNA extraction steps, the lysed subsamples are then each combined with a neutralization buffer and a high concentration of modified oligonucleotide primers, briefly heat treated and cooled, combined with an enzyme solution, and incubated under isothermal conditions to generate an amplified product. Amplified products are optionally divided to generate aliquots, which can be screened for the presence of at least one non-maternal allele. The amplified products, or unscreened aliquots of amplified products, are then optionally pooled to minimize bias arising from random events occurring in the single reactions, and subjected to array comparative genomic hybridization (array CGH) or sequencing to detect the presence of a fetal genetic variation. Quality control is optionally performed on the amplification, array CGH, and/or sequencing products to determine the quantity and/or quality of the products generated using the method of the embodiment.

In some embodiments, following amplification, the amplified products, or unscreened aliquots of amplified products, are then optionally pooled prior to performing a second amplification. In other embodiments, the products from the second amplification are optionally pooled to minimize bias arising from random events occurring in the single reactions, and subjected to array CGH or sequencing to detect the presence of a fetal genetic variation. Quality control is optionally performed on an amplification, array CGH product, and/or sequencing to determine the quantity and/or quality of the products generated using the method of the embodiment.

In some embodiments, the methods described herein are performed in a high throughput manner. In particular embodiments, at least, or at least about 96, 100, 192, 200, 288, 384, 400, 500, 600, 700, 800, 900, 1,000, 2,000, 3,000, 4,000, 5,000, 6,000, 7,000, 8,000, 9,000, or 10,000 amplification reactions, or a range defined by any two of the preceding values, are performed. In a specific embodiment, at least, or at least about 300 amplification reactions are performed. In a more particular embodiment, at least, or at least about 10,000 amplification reactions are performed. In some embodiments, the methods described herein are performed with automated systems, such as computer-controlled nanoliter fluid dispensers. In particular embodiments, a dispenser provided by BioDot (Irvine, Calif.) is used.

In particular embodiments, at least, or at least about 96, 100, 192, 200, 288, 384, 400, 500, 600, 700, 800, 900, 1,000, 2,000, 3,000, 4,000, 5,000, 6,000, 7,000, 8,000, 9,000, or 10,000 sequencing reactions, or a range defined by any two of the preceding values, are performed. In a specific embodiment, at least, or at least about 300 sequencing reactions are performed. In a more particular embodiment, at least, or at least about 10,000 sequencing reactions are performed.

As used herein, an "oligonucleotide" means a polymer of nucleotides. As used herein, "nucleotide" or "nucleic acid" means a deoxyribonucleic acid (e.g., DNA, mtDNA, gDNA, or cDNA), ribonucleic acid (e.g., RNA or mRNA), or any other variant of nucleic acids known in the art, including, for example, nucleic acid analogues such as peptide nucleic acids (PNAs), locked nucleic acids (LNAs), glycol nucleic acids (GNAs), and threose nucleic acids (TNAs). In some embodiments, the oligonucleotides described herein are single-stranded nucleic acids, double-stranded nucleic acids, small interfering ribonucleic acids (siRNA), or microRNAs (miRNA).

As used herein, "genetic amplification" refers to increasing the amount of genetic material. As used herein, "whole genomic amplification" refers to genetic amplification of substantially all of the genome of a cell. It is understood that these terms encompass amplification of the genetic material or genome that is modified from its natural state prior to amplification. As used herein, reference to whole genome amplification mixtures, buffers, or other solutions, are understood to also apply to mixtures, buffers, or solutions used for genetic amplification, and vice versa.

As used herein, "genetic variation" means any variation in a nucleic acid sequence. Genetic variations can range from a single base pair variation to a chromosomal variation, or any other variation known in the art. Genetic variations can be simple sequence repeats, short tandem repeats, single nucleotide polymorphisms, translocations, inversions, deletions, duplications, or any other copy number variation. In some embodiments, the chromosomal variation is a chromosomal abnormality. For example, the chromosomal variation can be aneuploidy, inversion, translocation, deletion, or duplication. A genetic variation can also be mosaic. For example, the genetic variation can be associated with genetic conditions or risk factors for genetic conditions (e.g., cystic fibrosis, Tay-Sachs disease, Huntington disease, Alzheimer disease, and various cancers). Genetic variations can also include any mutation, chromosomal abnormality, or other variation known to those of skill in the art (e.g., aneuploidy, microdeletion, or microduplication). Genetic variations can have positive, negative, or neutral effects on phenotype. For example, chromosomal variations can include advantageous, deleterious, or neutral variations. In some embodiments, the genetic variation is a risk factor for a disease or disorder. However, in some embodiments, the genetic variation encodes a desired phenotypic trait.

In some embodiments, the genetic variation is part of a panel for detecting a genetic disorder. For example, in some embodiments, the genetic variation is part of panel used during pre-implantation genetic diagnosis. In some embodiments, a maternal and/or paternal sample is tested for a genetic variation prior to testing in an offspring sample. For example, in some embodiments, carrier status for a disorder is determined for one or both parents prior to testing an embryo. In some embodiments, carrier status for a disorder is determined for one or both parents prior to testing a fetal cell from a biological sample comprising a mixture of maternal and fetal cells. In some embodiments, a maternal and/or paternal sample is tested for a genetic variation at the same time as testing in an offspring sample.

In some embodiments, the genetic variation is informative for a single gene disorder. In some embodiments, the genetic variation is informative for a complex genetic disorder. In some embodiments, the genetic variation is a marker for an American Congress of Obstetricians and Gynecologists (ACOG)-recommended disorder. In some embodiments, the genetic variation is a marker for an American College of Medical Genetics (ACMG)-recommended disorder. In some embodiments, the genetic variation is a known variation. In some embodiments, the genetic variation is a novel variation.

Sample Preparation for Isothermal Whole Genome Amplification

Cell Lysis

In some embodiments, a biological sample is diluted to achieve a desired cell concentration prior to cell lysis. In some embodiments, the cell concentration is about 10 cells per reaction volume. In a specific embodiment, the cell concentration is about 1 cell per reaction volume. For example, the cell concentration can be about 1 cell per reaction volume, where the reaction volume is 1 microliter. In some embodiments, the biological sample contains target and non-target cells. In some embodiments, the cells are nucleated cells. In some embodiments, the cells are human cells. For example, in some embodiments, the biological sample is a maternal sample containing maternal and fetal cells. In some embodiments, the single cell in a dilution is a fetal cell.

Oligonucleotides can be added to a reaction mixture prior to cell lysis. In some embodiments, the oligonucleotides reduce the loss of target DNA. For example, oligonucleotides can be present in an amount effective to reduce the adherence of DNA to its surroundings (such as the walls of a well or the surface of a slide) following release from a cell. In some embodiments, oligonucleotides serve to protect target genomic DNA after it is released from a cell. For example, oligonucleotides can be present in an amount effective to protect DNA from degradation by endogenous nucleases. In addition, oligonucleotides can be present in an amount effective to render DNA more accessible to primers in subsequent reactions, such as amplification reactions. In some embodiments, the oligonucleotides in a cell lysis solution also serve as the primers for an amplification reaction. For example, in some embodiments, oligonucleotides are only added prior to a cell lysis reaction. In other embodiments, oligonucleotides are added prior to both a cell lysis reaction and an amplification reaction. In some of these embodiments, the oligonucleotides used for the cell lysis and the primers for the amplification reaction are the same oligonucleotides. In other embodiments, the oligonucleotides used for the cell lysis and the primers for the amplification reaction are different oligonucleotides. In some embodiments, oligonucleotides are only added prior to an amplification reaction. In some embodiments, the oligonucleotides used in the methods and compositions in embodiments of the present invention are random oligonucleotides.

In some embodiments, the oligonucleotides are added to a cell dilution solution or a cell lysis buffer solution. In some embodiments, about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or 200 uM of oligonucleotides, or a range defined by any two of the preceding values, are present during cell lysis. In particular embodiments, about 5 uM to about 100 uM of added oligonucleotides are present during cell lysis. In more particular embodiments, about 10 uM to about 50 uM of random oligonucleotides are present during cell lysis. In specific embodiments, about 12 uM of random oligonucleotides are present during cell lysis.

In some embodiments, the oligonucleotides are about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases in length, or a range defined by any two of the preceding values. In particular embodiments, the oligonucleotides are about 4 bases to about 30 bases in length. In more particular embodiments, the oligonucleotides are about 7 bases to about 20 bases in length. In specific embodiments, the oligonucleotides are about 9 bases in length.

In some embodiments, a commercially available cell lysis buffer is used, such as an ABI lysis buffer designed for use in RT-PCR (ABI DNA Extract All Reagent Lysis Solution, Part No. 4405921). In some embodiments, the cell lysis buffer is an alkaline lysis buffer. In some embodiments, the cell lysis buffer is a phosphate-based buffer, such as a sodium phosphate-based or potassium phosphate-based buffer. In some embodiments, the cell lysis buffer contains the combination of a base and a reducing agent. In some embodiments, the cell lysis buffer contains the combination of a base, a reducing agent, and a chelator. In some embodiments, the cell lysis buffer does not contain a chelator. In some embodiments, the concentration of the base in the cell lysis buffer is, or is about 100, 150, 200, 250, 300, 350, 400, 450, 500, 550, 600, 650, 700, 750, 800, 850, 900, 950, or 1000 mM, or a range defined by any two of the preceding values. In some embodiments, the base is potassium hydroxide (KOH) or sodium hydroxide (NaOH). In some embodiments, the concentration of the reducing agent in the cell lysis buffer is, or is about 5, 10, 15, 20, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 mM, or a range defined by any two of the preceding values. In some embodiments, the reducing agent is selected from the group consisting of dithiothreitol (DTT), β-mercaptoethanol, and (tris(2-carboxyethyl)phosphine)) (TCEP). In some embodiments, the concentration of chelator in the cell lysis buffer is, or is about 0.5, 1, 1.5, 2, 2.5, 3, 3.5, 4, 4.5, 5, 6, 7, 8, 9, 10, 11, 12, 13, 14, 15, 16, 17, 18, 19, or 20 mM, or a range defined by any two of the preceding values. In some embodiments, the chelating agent is a divalent ion chelator. In some embodiments, the chelating agent is ethylenediaminetetraacetic acid (EDTA) or ethylene glycol tetraacetic acid (EGTA). In some embodiments, the cell lysis buffer contains the combination of potassium hydroxide (KOH), dithiothreitol (DTT), and EDTA. In some embodiments, the cell lysis buffer contains the combination of KOH and DTT. For example, in some embodiments, a cell lysis buffer containing 600 mM KOH, 25 mM DTT, and 2.5 mM EDTA; 600 mM KOH, 50 mM DTT, and 10 mM EDTA; 200 mM KOH, 50 mM DTT, and 2.5 mM EDTA; 200 mM KOH, 63 mM DTT, and 2.5 mM EDTA; 400 mM KOH, 100 mM DTT, and 10 mM EDTA; 600 mM KOH, 50 mM DTT, and 2.5 mM EDTA; 540 mM KOH, 50 mM DTT, and 2.5 mM EDTA; 600 mM KOH, 100 mM DTT, and 2.5 mM EDTA; 600 mM KOH, 25 mM DTT, and 10 mM EDTA; 200 mM KOH and 75 mM DTT; or 200 mM KOH and 83 mM DTT is used. In some embodiments, the cell lysis buffer does not contain EDTA or EGTA. In a particular embodiment, the cell lysis buffer does not contain EDTA. As discussed herein, in some embodiments, the cell lysis buffer contains oligonucleotides. Further, in some embodiments, the cell lysis buffer further contains any suitable protease, such as, for example, proteinase K.

In some embodiments, cell lysis is performed for about 2, 3, 4, 5, 10, 15, 20, 25, or 30 minutes, or a range defined by any two of the preceding values. In particular embodiments, cell lysis is performed for about 5 to about 10 minutes. In some embodiments, cell lysis is performed at about 4° C., 5° C., 6° C., 7° C., 8° C., 9° C., 10° C., 15° C., 20° C., 25° C., 30° C., 35° C., 40° C., 45° C., 50° C., 55° C., 60° C., or 65° C., or a range defined by any two of the preceding values. In specific embodiments, cell lysis is performed at room temperature.

Neutralization and Sample Preparation

Following lysis, a solution is added to neutralized the pH of the lysis buffer. In some embodiments, a commercially available neutralization buffer is used, such as an ABI buffer designed for use in RT-PCR (e.g., ABI DNA Extract All Reagent, Stabilization Solution, Part No. 4405928). In some embodiments, the neutralization buffer contains a phosphate salt and a chelator. In some embodiments, the neutralization buffer contains a phosphate salt, a chelator, and Tris. In some embodiments, the concentration of phosphate salt is, or is about 5, 10, 15, 20, 25, 30, 35, 40, 45, 50, 55, 60, 65, 70, 75, 80, 85, 90, 95, or 100 mM, or a range defined by any two of the preceding values. In particular embodiments, the concentration of phosphate salt is, or is about 25 mM to about 75 mM. In more particular embodiments, the concentration of the phosphate salt is, or is about 40 mM to about 60 mM. In specific embodiments, the concentration of the phosphate salt is, or is about 50 mM. In some embodiments, the phosphate salt is selected from the group consisting of sodium phosphate ($NaPO_4$), magnesium phosphate ($MgPO_4$), and potassium phosphate ($KPO_4$). In some embodiments, the concentration of the chelator is, or is about 0.1, 0.2, 0.25, 0.3, 0.4, 0.5, 1, 1.5, 2, 2.5, 3, 3.5, 4, 4.5, 5, 6, 7, 8, 9, or 10 mM, or a range defined by any two of the preceding values. In particular embodiments, the concentration of the chelator is, or is about 0.25 mM to about 5 mM. In more particular embodiments, the concentration of the chelator is, or is about 0.5 mM to about 1.5 mM. In specific embodiments, the concentration of the chelator is about 1 mM. In some embodiments, the chelator is a divalent ion chelator. In some embodiments, the chelator is EDTA or EGTA. In some embodiments, the concentration of Tris in the neutralization buffer is, or is about 5, 10, 15, 20, 25, 30, 35, 40, 45, 50, 55, 60, 65, 70, 75, 80, 85, 90, 95, or 100 mM, or a range defined by any two of the preceding values. In particular embodiments, the concentration of Tris is about 25 mM to about 75 mM. In more particular embodiments, the concentration of Tris is about 40 mM to about 60 mM. In specific embodiments, the concentration of Tris is about 50 mM. In some embodiments, the neutralization buffer contains oligonucleotides. In some embodiments, the concentration of oligonucleotides is, or is about 25, 50, 75, 100, 125, 150, 155, 160, 165, 170, 175, 180, 185, 190, 195, 200, 225, 250, 275, 300, 325, 350, 375, 400, 425, 450, 475, 500, 600, 700, 800, 900, or 1000 uM, or a range defined by any two of the preceding values. In particular embodiments, the concentration of oligonucleotides is about 100 uM to about 500 uM. In more particular embodiments, the concentration of oligonucleotides is about 150 uM to about 300 uM. In specific embodiments, the concentration of oligonucleotides is about 100 uM to about 300 uM. For example, in some embodiments, neutralization buffer containing $NaPO_4$, HCl, and oligonucleotide primers; 50 mM Tris and 200 uM oligonucleotides; or 50 mM $KPO_4$, 1 mM EDTA, and 200 uM oligonucleotides is used. Other neutralization buffers available to one skilled in the art can also be used. In some embodiments, the pH of the neutralization buffer is, or is about 7.4, 7.5, 7.6, 7.7. 7.8, 7.9, or 8.0, or a range defined by any two of the preceding values. In particular embodiments, the pH of the neutralization buffer is about 7.5 to about 7.9.

The neutralized mixture can be briefly heat denatured prior to an amplification reaction to further enhance DNA release from lysed cells (e.g., by helping large, complex genomic DNA molecules to release from lysed cells) and/or enhance primer-target DNA interactions while maintaining high quality amplification products. In some embodiments, a neutralized mixture is heat treated for less than about 1, 2, 3, 4, 5, 6, 7, 8, 9, 10, 11, 12, 13, 14, or 15 minutes, or a range defined by any two of the preceding values. In particular embodiments, a neutralized mixture is heat treated for less than about 2 minutes. In some embodiments, a neutralized mixture is heat treated at about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., or 99° C., or a range defined by any two of the preceding values. In particular embodiments, the neutralized mixture is heat treated at about 90° C. to about 99° C. In more particular embodiments, the neutralized mixture is heat treated at about 95° C. for about 1 minute. In some embodiments, the heat treated solution is immediately cooled, particularly on ice, to enhance primer-target genomic DNA interactions. As shown in Example 4, short heat denaturation times unexpectedly minimized damage to genetic material (e.g., compared to heat denaturation times used in standard protocols) while enhancing DNA release from lysed cells and enhancing primer-target genomic DNA interactions.

In some embodiments, cell lysis and amplification are performed without an intervening DNA extraction step. In some embodiments, cell lysis and amplification are performed in the same sample mixture. In specific embodiments, cell lysis and amplification are performed in the same location. For example, in some embodiments, cell lysis and amplification are performed in the same well or on the same slide. In some embodiments, the well is a microwell. In some embodiments, cell lysis and amplification are performed in the same emulsion solution.

In some embodiments, mechanical manipulation of samples is minimized. For example, in some embodiments, the mechanical manipulation of samples is minimized by reducing or eliminating vortexing of cells and/or extracted genomic material. For example, vortexing can be minimized during the preparation of samples for cell lysis or amplification. In particular embodiments, vortexing is eliminated from the preparation of a sample for a reaction. For example, a shaker, rotator, or manual inversion of a sample can be used. In some embodiments, no mixing of reagents or genetic material is used. Further, in some embodiments, a brief heat denaturation step is used to reduce damage to genetic material caused by the heat denaturation steps used in standard protocols. In particular embodiments, a neutralized mixture is heat treated at about 95° C. for about 1 minute. In some embodiments, the heat treated solution is immediately cooled on ice to enhance primer-target genomic DNA interactions.

As discussed above, isolating genomic DNA from whole blood was previously thought to require extensive purification using standard protocols. However, as shown in Example 5, the presence of RBCs in the amplification methods provided herein unexpectedly did not inhibit Phi29 DNA polymerase. In fact, higher concentrations of RBCs in the WGA reactions in Example 5 reduced the locus dropout (LDO) and allele dropout (ADO) rates. In some embodiments, the amplification reactions described herein are performed without previous steps to remove red blood cells (RBCs) from a sample. In some embodiments, up to about 5, 50, 500, 1000, 2500, 5000, 10000, 15000, 20000, 25000, 30000, 35000, 40000, 45000, 50000, 75000, or 100000 RBCs, or a range defined by any two of the preceding values, are present per microliter of total amplification reaction volume. In some embodiments, about 500 to about 50000 RBCs are present per microliter of total amplification reaction volume. In specific embodiments, about 2500 to about 10000 RBCs are present per microliter of total amplification reaction volume. In particular embodiments, at least about 3500 RBCs are present per microliter of total amplification reaction volume. In certain embodiments, the amplification reactions are whole genome amplification reactions.

Maintaining the Integrity of Genetic Material

As discussed above, previous methods for sample preparation, cell lysis, and amplification conditions caused damage to genetic material that compromised WGA performance. By combining some or all of the methods of preparing samples described herein, high quality and quantities of genetic material can be prepared for use in a WGA reaction. For example, the integrity of genetic materials can be maintained by using optimized cell lysis buffers, using oligonucleotides in lysis solutions, minimizing or eliminating mechanical manipulation, and using a brief heat denaturation treatment.

Amplification

In some embodiments, the starting genomic material for amplification is genomic material from about 1, 2, 3, 4, 5, 6, 7, 8, 9, 10, 15, 20, 25, 50, 75, 100, 200, 300, 400, 500, 750, 1000, 1200, and 1500 cells, or a range defined by any two of the preceding values. In some embodiments, the starting genomic material for amplification is genomic material from about 1 to about 500 cells. In specific embodiments, the starting genomic material for amplification is genomic material from about 1 cell to about 100 cells. In specific embodiments, the starting genomic material for amplification is from not more than one nucleated cell. In particular embodiments, the starting genomic material for amplification is genomic material from about 1 cell.

In some embodiments, a single amplification reaction is performed. In some embodiments, more than one amplification reaction is performed to increase the amount of amplified product and/or reduce false positive results. In some embodiments, fresh reagents are added, and amplification is continued. In some embodiments, a second amplification is performed to increase the amount of genomic material required for sequencing or aCGH analysis (for example, where not enough material is generated from a first amplification to carry out aCGH). For example, in some embodiments, a portion of the amplified material from a first amplification is used as the starting material for a second reaction. In some embodiments, at least, or at least about 1%, 5%, 10%, 15%, 20%, 25%, 30%, 35%, 40%, 45%, 50%, 55%, 60%, 65%, 70%, 75%, 80%, 85%, 90%, 95%, 99%, or 100%, or a range defined by any two of the preceding values, of the amplified product from a first amplification is used as starting material for a second amplification reaction. In particular embodiments, about 5% to about 75% of the amplified product from a first amplification is used as starting material for a second amplification reaction. In a more preferred embodiment, about 25% to about 50% of the amplified product from a first amplification is used as starting material for a second amplification reaction. In specific embodiments, about 25% of the amplified product from a first amplification is used as starting material for a second amplification reaction. Further, additional rounds of amplification, a splitting/sub-round approach, or a successive/simultaneous/linked applications approach can be used if more or less amplified material is desired. In specific embodiments, the polymerase in the first amplification reaction is heat inactivated, and 1 ul of the reaction volume is diluted to 20 ul total volume. In particular embodiments, 25% of the reaction volume is used in a second amplification.

Tris-based buffer, MOPS, or HEPES, or any other appropriate buffers known to those of skill in the art, can be used in the WGA mixtures described herein. Further, any polymerase with strand displacement activity can be used. In some embodiments, the polymerase is an isothermal or thermostable polymerase. In some embodiments, the polymerase is Phi29 DNA polymerase or Bst polymerase. In specific embodiments, the polymerase is Phi29 DNA polymerase. In some embodiments, the WGA mixture contains a salt mixture. In some embodiments, the concentration of the NaCl is about 1 to about 100 mM. In some embodiments, the concentration of the $MgCl_2$ is about 1 to about 100 mM. In some embodiments, the concentration of the $(NH_4)_2SO_4$ is about 1 to about 100 mM. In some embodiments, the concentration of the Phi29 DNA polymerase is about 1 to about 100 units. In some embodiments, the concentration of the dNTPs is about 0.1 to about 5 mM. In some embodiments, the concentration of the oligonucleotides is about 50 to about 200 mM. In some embodiments, the salt mixture contains Tris-HCl; NaCl or KCl; $MgCl_2$ or $MnCl_2$; and $(NH_4)_2SO_4$. For example, in particular embodiments, a salt mixture containing 50 mM Tris-HCl, 10 mM NaCl, 10 mM $MgCl_2$, and 10 mM $(NH_4)_2SO_4$ is used. In specific embodiments, the WGA mixture contains a salt mixture, a polymerase, dNTPs, and oligonucleotide primers. In some embodiments, the WGA mixture further contains at least one of DTT and BSA. In specific embodiments, the WGA mixture contains a salt mixture, 5 mM DTT, 0.38 mM dNTPs, 0.012 mM olignonucleotide primers, 1 ng/uL BSA, and 0.05 uL Phi29 DNA polymerase per microliter. In particular embodiments, the WGA mixture contains Tris-HCl (pH 7.5 prior to addition to the lysate), NaCl, MgCl, $(NH_4)_2SO_4$, Phi29 DNA polymerase, dNTPs, and oligonucleotide primers.

The oligonucleotide primers used in the reactions described herein can be modified to prevent the polymerization of primer-primer duplexes, while still allowing for template-directed polymerization. Although modified oligonucleotide primers have been described in the art, they have not been used in low-level DNA amplification or single cell WGA reactions. The examples described herein demonstrate that modified oligonucleotide primers unexpectedly reduce the formation of template-independent non-specific product in low-level DNA amplification (including single cell reactions), thereby improving WGA product quality. In some embodiments, the primers are nonamers or 9-base random sequence oligonucleotide primers (N9). In some embodiments, the primers contain a spacer arm (e.g., C6, C12, or C18), an abasic site, or a reverse polarity nucleotide. In some embodiments, the primers contain a C3 spacer at the 5' end. In specific embodiments, the primers are random nonamers with a C3 spacer at the 5' end (i.e., C3-N9). In particular embodiments, the primers further include an additional single nucleotide attached at the 5' end the C3 spacer (i.e., N—C3-N9). However, one of skill in the art will recognize that the primers described herein can contain other modifications that create a polymerization block at the 5' end.

Modified bases that reduce modified-base or modified-base complement hybridizations can also be employed to reduce template-independent amplification events in the methods described herein. Modified bases can also stabilize duplex formation, and can therefore be used to balance AT and GC melting temperature in order to enhance annealing of short primers to a DNA template that is less dependent on primer GC-content, thereby minimizing amplification bias. In some embodiments, the modified base is a 2-amino-dA or pyrimidine analog. In a specific embodiment, the modified-base pairing combination is 2,6-diaminopurine and 5-(1-propynyl)-2'-deoxy-Uridine (DAP/pdU). However, any appropriate modified-base pair combination known to those of skill in the art can be used (Y. Lebedev, et al., Genetic Analysis—Biomolecular Engineering, 1996, 13, 15-21; L. E. Xodo et al., Nucleic Acids Res., 1991, 19, 5625-5631; B. C. Froehler et al., Tetrahedron Lett., 1992, 33, 5307-5310; I.V. Kutyavin, et al., Biochemistry, 1996, 35, 11170-11176; and H. K. Nguyen, et al., Nucleic Acids Res., 1997, 25, 3059-65).

Further, the degeneracy of modified primers used in the amplification methods described herein can be reduced. For example, primer degeneracy can be reduced to eliminate the generation of primer reverse complements (which are inherent to random synthesis products), or to balance the GC/AT probe content to minimize amplification bias. Techniques for reducing primer degeneracy are well known to those of skill in the art.

Inorganic phosphate (PPi) generated from dNTPs during amplification reactions is inhibitory to polymerase and decreases the efficiency of amplification. Thus, in some embodiments, a yeast inorganic pyrophosphatase (IPP) (New England Biolabs, Inc., Ipswich, Mass.) or a thermostable inorganic pyrophosphatase (TIPP) (New England Biolabs, Inc., Ipswich, Mass.) is added to an amplification reaction to improve performance and/or efficiency. In specific embodiments, an inorganic pyrophosphatase is added to a low volume (e.g., a nanoliter scale) amplification reaction. Further, in some embodiments, bovine serum albumin (BSA) is used as a polymerase stabilizer to increase the efficiency of an amplification reaction.

In some embodiments, the amplification reaction is performed in a low reaction volume. In some embodiments, the amplification reaction is performed on a nanoliter scale. In some embodiments, the amplification reaction is performed on a microliter scale. In some embodiments, the amplification reaction is performed in a total reaction volume of about 10, 25, 50, 75, 100, 150, 200, 250, 300, 350, 400, 450, 500, 550, 600, 650, 700, 750, 800, 850, 900, 950, 1000, 1050, 1100, 1150, 1200, or 1250 nL, or a range defined by any two of the preceding values. In some embodiments, the amplification reaction is performed in a total reaction volume of about 1, 1.5. 2. 2.5, 3, 3.5, 4, 4.5, 5, 5.5, 6, 6.5, 7, 7.5, 8, 8.5, 9, 9.5 or 10 uL, or a range defined by any two of the preceding values. In particular embodiments, the amplification reaction is performed in a total reaction volume of about 200 nL to about 5 uL. In more particular embodiments, the amplification reaction is performed in a total reaction volume of about 500 nL to about 2.5 uL. In specific embodiments, the amplification reaction is performed in a total reaction volume of about 1000 nL. In some embodiments, $H_2O$ is used to scale up the volume of genetic material, lysis buffer, neutralization buffer, and WGA mix to the total reaction volume. In particular embodiments, the ratio of components in the final composition for a WGA reaction is 1:1:1:1:7 of genetic material:lysis buffer:neutralization buffer:$H_2O$:WGA mix.

In some embodiments, the final composition for amplification is incubated at about 4° C., 5° C., 6° C., 7° C., 8° C., 9° C., 10° C., 15° C., 20° C., 25° C., 30° C., 35° C., 40° C., 45° C., or 50° C., or a range defined by any two of the preceding values. In particular embodiments, the final composition for amplification is incubated at about 25° C. to about 40° C. In specific embodiments, the final composition for amplification is incubated at about 30° C. In some embodiments, the amplification involves incubation for at least, or at least about 1, 5, 10, 15, 30, 45, or 60 minutes, or a range defined by any two of the preceding values. In some embodiments, the amplification involves incubation for at least, or at least about 1.5, 2, 2.5, 3, 3.5, 4, 4.5, 5, 6, 7, 8, 9, 10, 11, 12, 13, 14, 15, 16, 17, 18, 19, 20, 21, 22, 23, or 24 hours, or a range defined by any two of the preceding values. In particular embodiments, a mixture is incubated for about 30 minutes to about 4 hours. In more particular embodiments, a mixture is incubated for at least about 3 hours.

Pooling

Random events, such as genomic template damage, random priming bias, and allele and locus dropout, do not occur equally in WGA reactions. WGA products are therefore pooled in some embodiments to normalize the effects of random events. In some embodiments, multiple reactions from the same source (such as a clinical sample, cell population, or cell type) are pooled. In some embodiments, reactions from different sources are pooled. In some embodiments, equal masses of amplification products are pooled to minimize the influence or bias a single reaction could have on the pool if the reaction yield is either very low or high. In some embodiments, about 2, 3, 4, 5, 10, 15, 20, 25, 50, or 100 reactions, or a range defined by any two of the preceding values, are pooled. In particular embodiments, about 2 to about 50 reactions are pooled. In more particular embodiments, about 2 to about 20 reactions are pooled. In specific embodiments, about 5 reactions are pooled.

Sample pooling strategies can be used following a first and/or a second WGA reaction. In some embodiments, products from multiple first WGA reactions are pooled prior to performing a second WGA. In some embodiments, products from multiple second WGA reactions are pooled prior to performing an analysis. In some embodiments, products from multiple first WGA reactions are pooled prior to performing a second WGA, and products from multiple second WGA reactions are pooled prior to performing an analysis. In some embodiments, products from first and second WGA reactions are pooled prior to performing an analysis.

Products from WGA reactions can also be divided into aliquots in conjunction with pooling strategies. For example, the product from a first WGA reaction can be aliquoted into multiple portions, with each portion undergoing a second WGA reaction, followed by pooling of the products from the second WGA reaction prior to an analysis. In some embodiments, the aliquots of products from multiple first WGA reactions are pooled, and a second WGA reaction is performed on the pooled products. Alternatively, the products or aliquots thereof from multiple first WGA reactions can be pooled, then re-split into multiple reactions prior to a second round of WGA reactions. In some embodiments, samples are pooled following a second WGA reaction and prior to an analysis.

Targeted pooling strategies can also be used. In some embodiments, samples identified as containing a fetal cell are pooled. For example, samples from a WGA reaction can be divided into aliquots, where at least one aliquot from each sample is tested for the presence of a fetal allele, and where at least one remaining aliquot from each sample identified as containing a fetal cell is pooled. In some embodiments, the pooled sample is tested for a genetic variation. In some embodiments, the pooled sample undergoes an additional WGA reaction. In some embodiments, samples demonstrating a particular level of quality are pooled. For example, samples from a WGA reaction can be divided into aliquots, where at least one aliquot from each sample is tested for ADO or LDO, and where at least one remaining aliquot from each sample identified as generating an ADO or LDO rate below a particular value is pooled. One of skill in the art will also recognize other variations to the pooling strategies can be performed in combination with the methods described herein.

Array Comparative Genomic Hybridization

In some embodiments, array CGH is used to identify the presence of a genetic variation in a sample following WGA. For example, in some embodiments, array CGH is used to analyze copy number variation (CNV) to detect an aneuploidy. In a preferred embodiment, array CGH is used to identify a genetic variation associated with a genetic condition or a risk factor for a genetic condition.

Further, in some embodiments, the quality and/or quantity of WGA products are evaluated using array CGH as described herein. As discussed herein, standard protocols for isothermal WGA on single cell genomic material have resulted in unacceptable levels of "noise" on array CGH, for example, an increased spread in the data points on a log ratio plot. The methods and compositions described herein unexpectedly generate low levels of noise on array CGH with WGA products from a single cell, as shown in Example 2.

Sequencing

In some embodiments, sequencing is used to identify the presence of a target cell and/or genetic variation in a sample following WGA. For example, in some embodiments, sequencing is used to identify a genetic variation associated with a genetic condition or a risk factor for a genetic condition.

In some embodiments, the sequencing method is a next generation sequencing method. For example, in some embodiments, the sequencing is performed using a platform such as the Illumina Genome Analyzer, Roche 454 Sequencer, Applied BioSystems SOLiD instrument, Ion-Torrent Personal Genome Machine, Heliscope instrument (Helicos Biosciences Corporation, Cambridge, Mass.), Single Molecule Real Time (SMRT) DNA sequencing technology (Pacific Biosciences, Menlo Park, Calif.) or Nanostring technology (Nanostring Technologies, Seattle, Wash.), However, sequencing can be performed using any appropriate technique or platform known to those of skill in the art.

Quality Control

Quality can be assessed for any of the products described herein, including products from a single cell reaction, pooled products from single cell reactions, products from reactions performed using multiple cells, or pooled products from reactions performed using multiple cells.

In some embodiments, the quality of a WGA product is measured by the ability to identify a target locus using standard methods, such as SNP genotyping or sequencing analysis. SNP genotyping or sequencing can also be used to measure the level of coverage of the genome using the methods described herein.

In some embodiments, the quality of a WGA product is measured using allele dropout (ADO) or locus dropout (LDO) rates. For example, quality can be measured by genotyping the products of WGA reactions for known heterozygous SNPs and determining the fraction of these heterozygous loci that generate a homozygous (i.e., ADO) or non-detectable (i.e., LDO) result. In some embodiments, PCR-based, SNP array-based, array CGH-based, or sequencing-based approaches are used to quantify a reduction in ADO or LDO rates compared to ADO or LDO rates generated using standard methods. For example, in some embodiments, the quality of a WGA product is measured by the quality of array CGH data generated using the WGA product. For example, in some embodiments, a high quality WGA product can be determined by identifying a reduction in "noise" on array CGH (e.g., a reduction in the spread of the data points on a log ratio plot). In addition, improved quality can also be measured by any appropriate technique known to those of skill in the art.

Further, improved performance of the methods described herein can be measured as increased amplification from specific genomic material of interest, decreased (or elimination of) amplification from template-independent polymerization, less biased amplification of genomic material of interest, or any other appropriate method known the those of skill in the art. In some embodiments, the reduction in bias is measured as a reduction in the ADO rate of a marker of at least, or at least about, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99%, or a range or a range defined by any two of the preceding values as compared to a standard WGA, for example, a WGA disclosed in Morrison et al., *Am J Trop Med Hyg.* 76 (2007) 1132-1137), Genomic Protocols, or Current Protocols in Molecular Biology. In some embodiments, the reduction in bias is measured as a reduction in the ADO rate of a marker of at least, or at least about, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99%, or a range or a range defined by any two of the preceding values. An 80% reduction in the ADO rate is shown in Example 8. In some embodiments, the ADO rate is less than about 1, 2, 3, 4, 5, 6, 7, 8, 9, 10, 15, 20 25, 50% of amplification reactions.

It will be understood by those of skill in the art that numerous and various modifications can be made without departing from the spirit of the present invention. Reagents and protocols known to those of skill in the art can be found, for example, in Genomic Protocols and Current Protocols in Molecular Biology (Genomic Protocols, vol. 439, Starkey and Elaswarapu ed., Totowa, N.J.: Humana Press Inc.; Current Protocols in Molecular Biology© 2008: John Wiley & Sons, Inc.). All the references referred to herein are incorporated by reference in their entirety for the subject matter discussed. The following examples are included for illustrative purposes only and are not intended to limit the scope of the invention.

EXAMPLE 1

Decreased Template-Independent Polymerization in Whole Genome Amplification

The effect of modified primers on template-independent polymerization in WGA was examined as follows. Approximately 0.2 ng of female genomic DNA (224.9 ng/uL) (Promega; Madison, Wis.) was combined with either standard random nonamer primers or modified random nonamer primers in Tris (pH 7.5) and KCl buffer in 10 uL or 25 uL final volumes. A primer annealing reaction was carried out by heating the mixtures for 3 minutes at 95° C. and then snap cooling on ice for 5 minutes. Following cooling, either 10 uL or 25 uL of a WGA mix (consisting of phi29; 2× supplied phi29 reaction buffer; dNTPs (New England Biolabs, Ipswich, Mass.); BSA (Promega, Madison, Wis.); and Yeast Inorganic Pyrophosphatase (New England Biolabs, MA)) was added to the DNA/primer mixture and incubated for 4 hours at 30° C., followed by a heat inactivation step at 65° C. for 10 minutes.

Following heat inactivation, 10 uL of each WGA reaction was run on a 0.8% agarose gel in 1×TBE buffer (Invitrogen, Carlsbad, Calif.). The gel was then stained with ethidium bromide and imaged on a UV light box.

As seen in FIGS. 1A and 1B, use of modified primers in WGA resulted in a reduction in the generation of template-independent polymerization products as compared to the amount of template-independent polymerization products observed using control primers. Additionally, use of modified primers in WGA in low reaction volumes resulted in improved amplification (see FIG. 1B).

These results showed that the methods and compositions in embodiments of the present invention are useful for decreasing template-independent polymerization in a whole genome amplification. These results suggested that the methods and compositions in embodiments of the present invention are useful for whole genome amplification.

EXAMPLE 2

Improved Whole Genome Amplified Genomic Material by Array Comparative Genomic Hybridization Array comparative genomic hybridization (aCGH) is a technique that allows for the detection of DNA sequence copy number aberrations throughout the genome (e.g., chromosomal imbalance, aneuploidy). aCGH can also be used to evaluate the efficacy of a WGA method. Accordingly, aCGH analysis was used to evaluate the efficacy of the WGA methods in embodiments of the present invention compared to standard WGA methods as follows.

As a reference, aCGH analysis was performed on DNA produced according to standard WGA techniques. Briefly, ten cells from two cell lines, AG09802 and GM10175 (Coriell Institute for Medical Research; Camden, N.J.), were dispensed independently into separate wells on a 384-well plate and incubated with a standard lysis buffer (Lysis Solution; Applied Biosciences, Foster City, Calif.) at room temperature for 3 minutes. Following lysis, a standard neutralization buffer (Stabilization Solution, Applied Biosciences, Foster City, Calif.) was added to each well for 3 minutes. Next, a first isothermal WGA was carried out using phi29 polymerase (Enzymatics, Beverly, Mass.), standard random nonamer primers (Integrated DNA Technologies, Inc., Coralville, Iowa), and Yeast Inorganic Pyrophosphatase (New England Biolabs, Ipswich, Mass.) in a 1 uL final volume reaction for 4 hours at 30° C., followed by a 65° C. heat inactivation step for 10 minutes. The 1 uL WGA samples were then subjected to a second isothermal WGA using phi29 polymerase by adding 4 uL of a random nonamer primer/annealing Tris-buffer mix. After heating for 3 minutes at 95° C., the 5 uL reaction volumes were cooled on ice for 5 minutes before adding 5 uL of a WGA mix (consisting of phi29; 2× supplied phi29 reaction buffer; dNTPs (New England Biolabs, Ipswich, Mass.); BSA (Promega, Madison, Wis.); and Yeast Inorganic Pyrophosphatase (New England Biolabs, MA)). The second isothermal WGA was then carried out for 4 hours at 30° C., followed by a 10 minute heat inactivation step at 65° C.

The 10 uL samples from the second WGA were then restriction enzyme digested, labeled, DTR-column purified (Edge BioSystems, Gaithersburg, Md.), paired, and hybridized on an Agilent 8×60 k CGH array according to the manufacturer's protocol. After washing and scanning the aCGH slides according to the manufacturer's protocol, the data was analyzed using Nexus 5.0 software from BioDiscovery (El Segundo, Calif.).

In another set of experiments, aCGH analysis was performed on DNA produced by methods and compositions in embodiments of the present invention. Briefly, 10 cells from two cell lines, AG09802 and GM10239 (Coriell Institute for Medical Research, Camden, N.J.), were dispensed independently into separate wells of a 384-well plate and incubated with a standard lysis buffer (Lysis Solution, Applied Biosciences, Foster City, Calif.) at room temperature for 3 minutes. Following cell lysis, a phosphate-based neutralization buffer in embodiments of the invention was added to each well for 3 minutes. Next, a first isothermal WGA was carried out using phi29 polymerase (Enzymatics, Beverly, Mass.), modified random nonamer primers (Integrated DNA Technologies, Inc., Coralville, Iowa), and Yeast Inorganic Pyrophosphatase (New England Biolabs, Ipswich, Mass.) in a 1 uL final volume reaction for 4 hours at 30° C., followed by a 65° C. heat inactivation step for 10 minutes. Following the first isothermal WGA, 19 uL of nuclease free water was added to the 1 uL WGA samples. Subsequently, 10 uL of the diluted WGA samples were subjected to a second isothermal WGA using phi29 polymerase by adding 2.5 uL of a modified random nonamer primer/annealing buffer mix. After heating for 3 minutes at 95° C., the 12.5 uL reaction volumes were cooled on ice for 5 minutes before adding 7.5 uL of a WGA mix (consisting of phi29; 2.67× supplied phi29 reaction buffer; dNTPs (New England Biolabs, Ipswich, Mass.); BSA (Promega, Madison, Wis.); and Yeast Inorganic Pyrophosphatase (New England Biolabs, MA)). The second WGA was then carried out for 4 hours at 30° C., followed by a 10 minute heat inactivation step at 65° C.

The 20 uL samples from the second WGA were then restriction enzyme digested, labeled, DTR-column purified (Edge BioSystems, Gaithersburg, Md.), paired, and hybridized on an Agilent 8×60 k CGH array according to the manufacturer's protocol. After washing and scanning the aCGH slides according to the manufacturer's protocol, the data was then analyzed using the Nexus 5.0 software from BioDiscovery (El Segundo, Calif.).

Figure 2A:
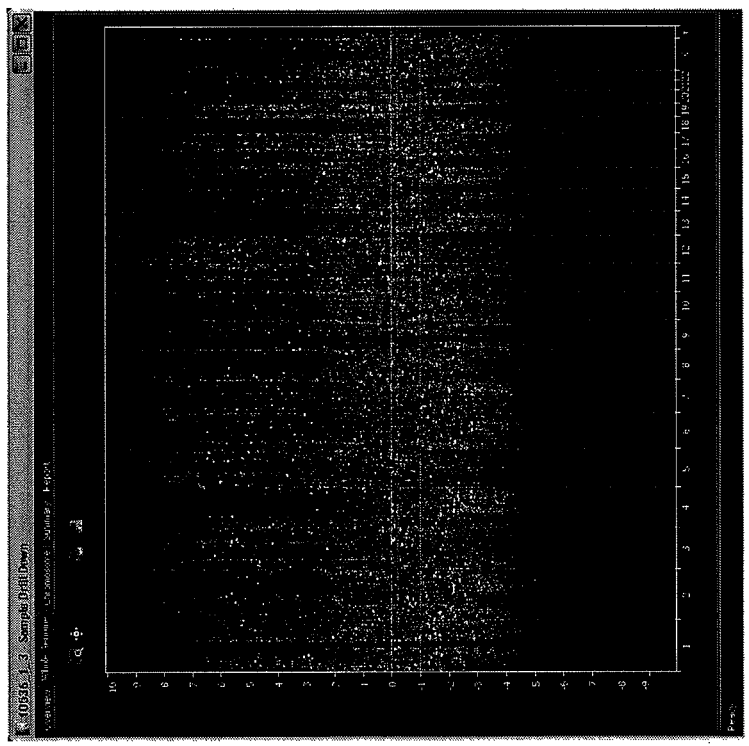

The results of aCGH analysis of genomic material produced by standard WGA is shown in FIG. 2A. As shown in FIG. 2A, standard WGA techniques were ineffective at amplifying low level genomic material (e.g., 10 cell genomes). A substantial amount of "noise" (e.g., the spread in the data points on the log ratio plot) was observed in genomic material produced by standard WGA methods which precluded the detection of genetic variation in the samples. FIG. 2B shows aCGH analysis of genomic material produced by the WGA methods in embodiments of the present invention. As shown in FIG. 2B, WGA using the methods and compositions in embodiments of the present invention were efficient at amplifying low level genomic material (e.g., 10 cell genomes) as compared to standard WGA methods. A substantial reduction in "noise" enabled the detection of genetic variation in the samples. Arrows in FIG. 2B denote chromosomal imbalances present in the sample genome.

These results indicated that methods and compositions in embodiments of the present invention are useful for performing whole genome amplification. More particularly, these results suggested that the methods and compositions in embodiments of the present invention are useful for whole genome amplification of low level genomic material (e.g., a single cell). These results further showed that the methods and compositions in embodiments of the present invention are useful for performing array comparative genomic hybridization and for identifying or detecting a genetic variation in a cell.

EXAMPLE 3

Pooling WGA Products Normalizes the Effects of Random Events

Random events, such as genomic template damage, random priming bias, and allele and locus dropout, do not occur equally in WGA reactions. Accordingly, the effect of pooling WGA products produced by the methods and compositions in embodiments of the present invention was examined as follows.

Ten cells or one cell of each of two cell lines, GM10239 and GM11962 (Coriell Institute for Medical Research, Camden, N.J.), were dispensed independently into separate wells of a 384-well plate and incubated with a lysis buffer (Lysis Solution, Applied Biosciences, Foster City, Calif.) at room temperature for 3 minutes. Following cell lysis, a phosphate-based neutralization buffer in embodiments of the invention was added to each well for 3 minutes. After a one minute 95° C. denaturation step, a first isothermal WGA was carried out using phi29 polymerase (Enzymatics, Beverly, Mass.) and modified random nonamer primers (Integrated DNA Technologies, Inc., Coralville, Iowa) in a 1 uL final volume reaction for 2 hours at 30° C., followed by a 65° C. heat inactivation step for 10 minutes. Following the first isothermal WGA, 19 uL of nuclease free water was added to the 1 uL WGA samples. Subsequently, 10 uL of the diluted WGA samples were subjected to a second isothermal WGA using phi29 polymerase by adding 2.5 uL of a modified random nonamer primer/annealing buffer mix. After heating for 3 minutes at 95° C., the 12.5 uL reaction volumes were cooled on ice for 5 minutes before adding 7.5 uL of a WGA mix (consisting of phi29; 2.67× supplied phi29 reaction buffer; dNTPs (New England Biolabs, Ipswich, Mass.); BSA (Promega, Madison, Wis.); and Yeast Inorganic Pyrophosphatase (New England Biolabs, MA)). The second WGA was then carried out for 4 hours at 30° C., followed by a 10 minute heat inactivation step at 65° C.

The 20 uL samples from the second WGA were then restriction enzyme digested in a 26 uL final volume using 5 units each of RsaI and AluI (Promega, Madison, Wis.) and the manufacturer's supplied buffer for 2 hours at 37° C., followed by a heat inactivation step of 65° C. for 20 minutes and then cooled on ice to 4° C. before DTR-column (Edge BioSystems, Gaithersburg, Md.) purifying according to manufacturer's protocol. After DTR purification, the DNA yield was quantified using the NanoDrop 1000 spectrophotometer (Thermo Scientific, Wilmington, Del.) according to manufacturer's instructions. Next, appropriate "pools" were made by pooling 5 uL of each of the appropriate individual post-DTR purified WGA reactions and these pooled samples were re-quantified using the NanoDrop 1000 spectrophotometer.

Next, 1 ug from each of the appropriate samples (unpooled and pooled) was labeled with an appropriate dye (cy3 or cy5) according to the Agilent microarray labeling protocol, DTR-column purified (Edge BioSystems, Gaithersburg, Md.) per manufacturer's instructions, appropriately paired for hybridization, and then hybridized on an Agilent 8×60 k CGH array according to the manufacturer's instructions. After washing and scanning the aCGH slides according to the manufacturer's instructions, the data was then analyzed using the Nexus 5.0 software from BioDiscovery (El Segundo, Calif.).

Figure 3A:
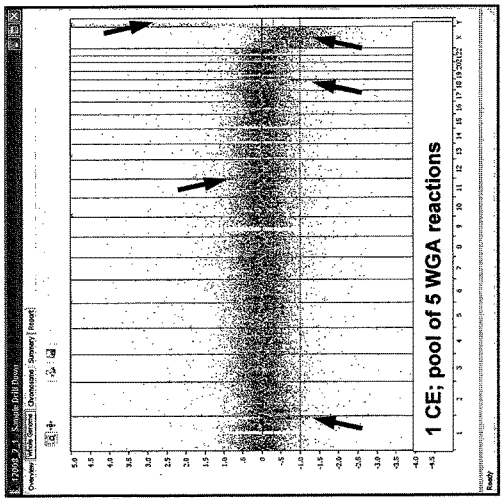
FIGS. 3A-3D set forth data from pooling methods of embodiments of the present invention showing normalized effects of random events from whole genome amplification.
Figure 3C:
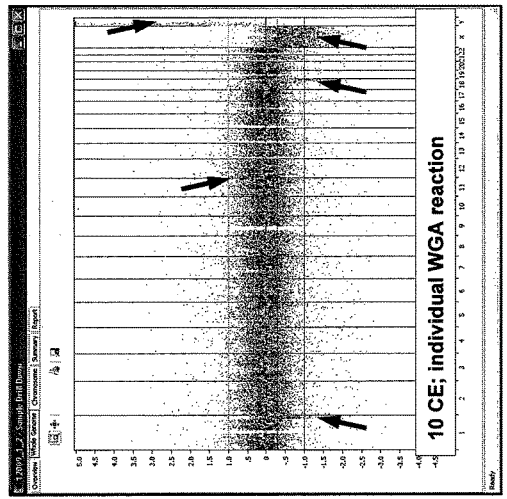
Figure 3B:
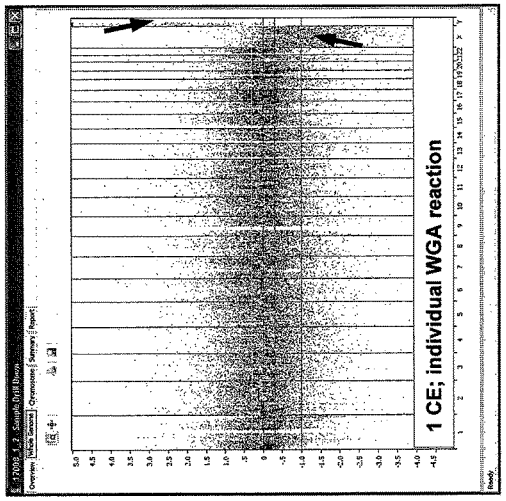
Figure 3D:
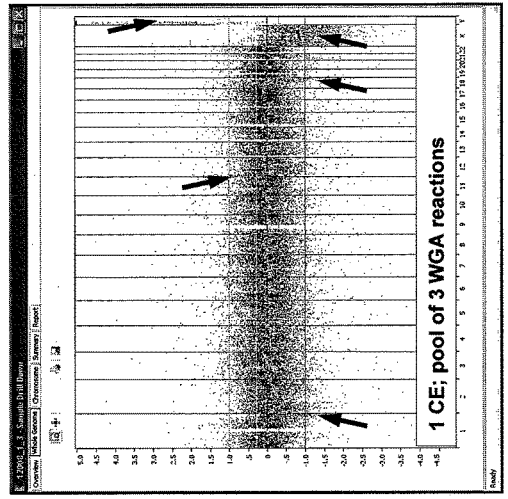

FIGS. 3A-3D show the results of aCGH analysis of pooled and non-pooled genomic material produced by WGA methods in embodiments of the present invention. As shown in FIG. 3A, non-pooled single cell genomic material produced by WGA methods in embodiments of the present invention allowed for whole chromosome imbalance detection. The pooled genomic material from three separate single cell WGA reactions in FIG. 3B show clear sub-chromosomal imbalance detection (i.e., aneuploidy). Pooling genomic material from five single cell WGA reactions showed a clear reduction in "noise" as compared to non-pooled single cell genomic material (compare FIG. 3A to FIGS. 3B and 3C). In particular, sub-chromosomal imbalance detection with five single cell pooled WGA samples was comparable to sub-chromosomal imbalance detection with ten cell non-pooled WGA samples (see FIGS. 3C and 3D).

These results showed that pooling WGA genomic material reduced noise and normalized the effects of random events in non-pooled WGA genomic material. Further, these results showed that the methods and compositions in embodiments of the present invention are useful for performing whole genome amplification. More specifically, these results showed that the methods and compositions in embodiments of the present invention are useful for performing array comparative genomic hybridization and for identifying or detecting a genetic variation in a cell.

EXAMPLE 4

Reduced Genomic Damage Improved Whole Genome Amplification

Genomic damage (e.g., fragmentation, nicking, etc.) can occur while preparing DNA for whole genome amplification. Accordingly, a model of heat-induced DNA damage was performed to examine the effects of genomic damage on WGA efficacy.

Approximately 500 ng of female or male genomic DNA (Promega, Madison, Wis.) in 50 uL of nuclease-free water was either heated (heat treatment) or not heated (control treatment) prior to further dilution to 1 ng/uL DNA in nuclease-free water. Heat treated samples were subjected to either a 99° C. for 4 minutes or 95° C. for 12.5 minutes before cooling on ice for 5 minutes and subsequently diluted to a final DNA concentration of 1 ng/uL. Following treatment, samples were subjected to isothermal amplification using phi29 polymerase and 1 ng of input DNA.

DNA samples were annealed in a 10 uL volume reaction with modified random nonamer primer formulation in 10 mM Tris (pH7.5) and 20 mM KCl. The primer annealing reaction was carried out by heating the reaction mix for 3 minutes at 95° C. and then cooled on ice for 5 minutes. Next, 10 uL of a WGA mix (consisting of phi29 (Enzymatics, Beverly, Mass.); 2× supplied phi29 reaction buffer; dNTPs (New England Biolabs, Ipswich, Mass.); BSA (Promega, Madison, Wis.); and Yeast Inorganic Pyrophosphatase (New England Biolabs, MA)) was added to the DNA/primer mixture and then incubated for 4 hours at 30° C., followed by a 10 minute heat inactivation step at 65° C.

Figures 4A, 4B:
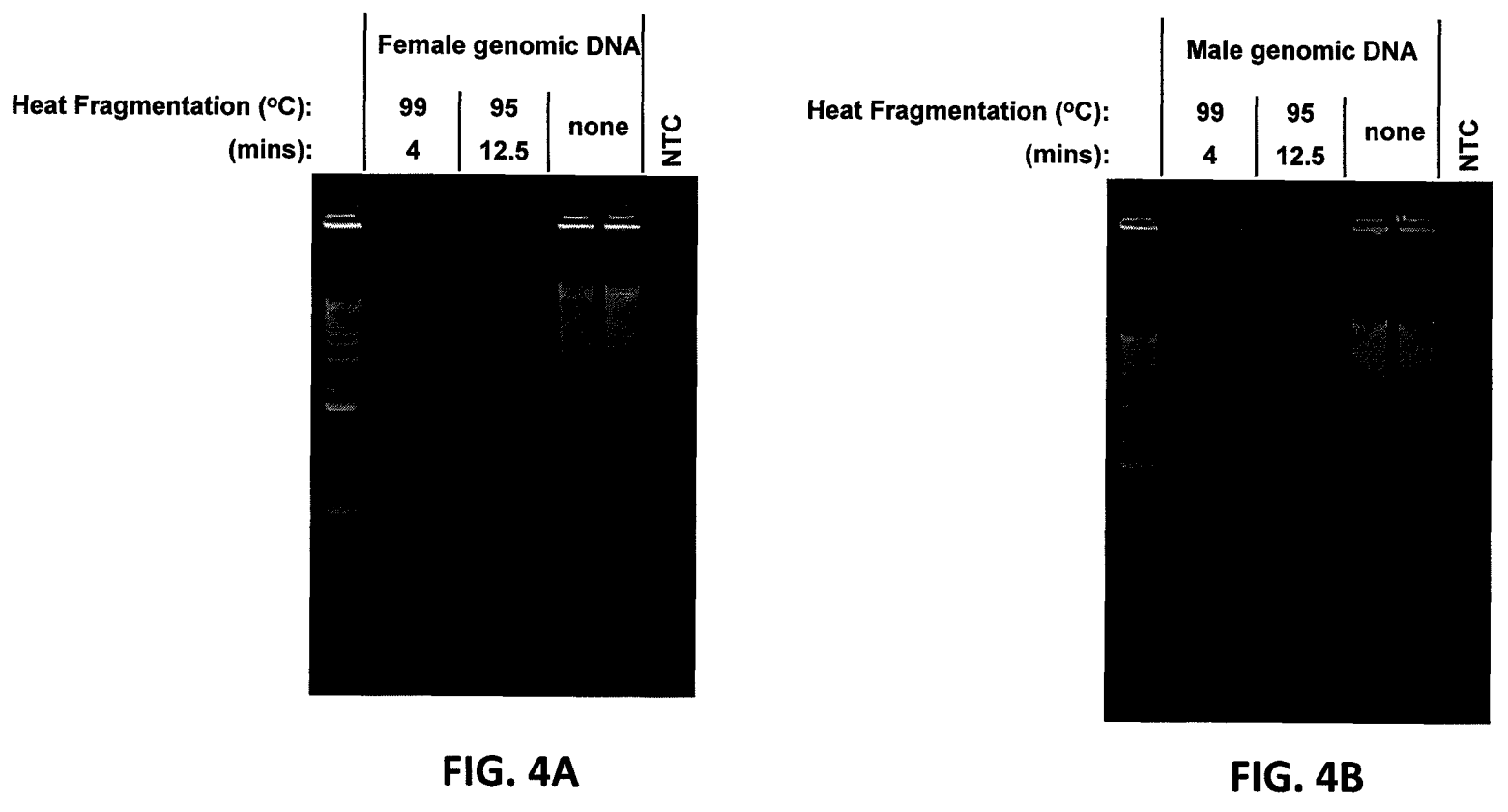

Following WGA, 3 uL of each reaction was run on a 0.8% agarose gel in 1× TBE buffer (Invitrogen, Carlsbad, Calif.) with 1 ug of a 1 kb molecular weight size marker (Invitrogen, Carlsbad, Calif.), denoted as "M" in FIGS. 4A and 4B. The gel was then stained with ethidium bromide before imaging on a UV light box.

These results suggested that the methods and compositions in embodiments of the present invention reduce genomic damage and improve whole genome amplification. Genomic damage (e.g., fragmentation, nicking, etc.) can occur from, for example, application of mechanical manipulation (e.g., vortexing) or increasing temperature (e.g., heating) of genomic material, therefore, these results suggested that heating genomic material at 95° C. for less than 12.5 minutes is useful for preparing DNA for whole genome amplification.

EXAMPLE 5

Red Blood Cells Improved the Quality of Whole Genome Amplified DNA

The effect of red blood cells (RBCs) on phi29 activity and the quality (e.g., yield, coverage) of whole genome amplified DNA was examined as follows.

RBCs were isolated from adult female peripheral blood using a Pall filter (Covina, Calif.), washed in PBS buffer, and mixed with target cells (cell line 12891, male) in various ratios. Subsequently, 100 nL of these cell solutions containing, on average, one 12891 cell with or without 500 to 50,000 RBCs (see FIG. 5), were dispensed into individual wells on a 384 PCR plate. Next, isothermal WGA was carried out on each sample according to the methods described for the first isothermal WGA in Example 2 above. Following WGA, 19 uL of nuclease-free water was added to each sample and approximately 0.5 uL of the diluted WGA product were subjected to PCR to compare the amplification yield and fidelity of target cell (12891) WGA, with and without RBCs in the reaction.

FIG. 5 shows PCR data from a biplex PCR detecting 2 loci, one from the X chromosome (X2) and one from the Y chromosome (SRY2). Introduction of RBCs to WGA reactions did not affect the Ct. values of either SRY2 or X2 (i.e., no reduction on amplification yield) and did not reduce the number of positive WGA reactions or the percentage of positive WGA reactions (or Poisson distribution of the single target cell 12891 in WGA). These results showed that RBCs, up to 50,000 RBCs in 1 uL WGA reaction, had no inhibitory effect on whole genome amplification of target genomic DNA from a single cell. Additionally, RBCs in WGA improved the fidelity of WGA, as evidenced by an increase in the number of WGA with both SRY2 and X2 detected (indicating no allele or locus dropout). In contrast, the number of WGA reactions with allele and loci dropout (those with no detection and single SRY2 or X2 detection) decreased with an increase of RBCs in the WGA reaction) (see FIG. 5). Another series of experiments was carried out on the above WGA samples with 18 heterozygous SNP PCR to the target cell (12891). A result of heterozygous genotype would indicate a successful amplification of both alleles, while a homozygous genotype would indicate allele dropout (ADO) and locus dropout (LDO) for no allele detection (ND). The results of the 18 heterozygous SNP PCR, including the percentage of ADO and LDO for each test group is shown in FIG. 6. These data demonstrate that the presence or addition of RBCs to WGA increased the heterozygous count (indicating improved quality of WGA product) but reduced the homozygous count (indicated reduced ADO) and ND (indicting reduced LDO) rates.

These results showed that the presence of RBCs in WGA reactions does not inhibit target genomic amplification, and in fact improves the coverage of target genomic WGA. The results further showed that the methods and compositions in embodiments of the present invention are useful for performing whole genome amplification.

EXAMPLE 6

Improved Coverage and Fidelity of Whole Genome Amplified DNA

Following cell lysis, whole cell lysates are generally neutralized using Tris-based buffers prior to WGA. Tris-based buffers can damage DNA resulting in reduced coverage and fidelity of whole genome amplified DNA. Accordingly, the effects of a modified neutralization buffer on performance of WGA were examined as follows. Single cells from two cell lines, AG09802 and GM10175 (Coriell Institute for Medical Research, Camden, N.J.), were dispensed independently into separate wells on a 384-well plate and incubated with a standard lysis buffer (Lysis Solution, Applied Biosciences, Foster City, Calif.) at room temperature for 3 minutes. Following lysis, half of the samples (96 wells) were neutralized with a Tris buffer and the other half of the samples (96 wells) were neutralized with a phosphate-based buffer in embodiments of the present invention for 3 minutes. Next, a first isothermal WGA was carried out using phi29 polymerase (Enzymatics, Beverly, Mass.), random nonamer primers (Integrated DNA Technologies, Inc., Coralville, Iowa), and Yeast Inorganic Pyrophosphatase (New England Biolabs, Ipswich, Mass.) in a 1 uL final volume reaction for 4 hours at 30° C., followed by a 65° C. heat inactivation step for 10 minutes.

WGA products from all reactions were analyzed by a biplex real-time PCR to detect specific products amplified from the Y chromosome ("DDY2") and GAPDH gene (glyceraldehyde-3-phosphate dehydrogenase, a house keeping gene). The presence of a single cell in each "positive" WGA reaction is necessary for determining the allele dropout (ADO) and loci dropout (LDO) rates in WGA. Accordingly, an appropriate Poisson distribution was used to deliver one cell or no cell to each well. The presence of a single cell in each WGA reaction was determined by the detection of either DDY2 and/or GAPDH gene products. WGA reactions with only GAPDH product detected indicated ADO for DDY2 on the Y chromosome from the cell in the WGA reaction. On the other hand, wells with only the DDY2 product detected indicated LDO for GAPDH gene in the WGA. The percentage of DO was calculated by dividing the number of DO with the total number of WGA wells with a cell.

Table 1 below summarizes the ADO and LDO rates for the two neutralization buffers tested. As shown in Table 1, a similar number of wells in each buffer group contained a single cell (71 for Tris buffer versus 73 for Phosphate-based buffer). WGA products from cell lysates neutralized with a Tris-based buffer showed an allele dropout rate of 20%. In contrast, WGA products from cell lysates neutralized with a Phosphate-based buffer reduced the allele dropout rate to 4% (see Table 1).

TABLE 1

| Neutralization buffer | Total WGA wells | No. of wells with cell | (%) of wells with cell | Wells with DDY2 DO | Wells with GAPDH DO | DDY2 DO Rate | GAPDH DO Rate |
|---|---|---|---|---|---|---|---|
| Tris HCl | 96 | 71 | 74% | 14 | 3 | 20% | 4% |
| KE | 96 | 73 | 76% | 3 | 2 | 4% | 3% |

These results showed that the methods and compositions in embodiments of the present invention are useful for improving coverage and fidelity of whole genome amplified DNA. These results further showed that the methods and compositions in embodiments of the present invention are useful for preparing DNA for whole genome amplification.

What is claimed is:

1. A method of whole genome amplification of genomic DNA from a cell, comprising:
    preparing a lysis mixture of:
        a sample comprising a cell containing genomic DNA and red blood cells;
        exogenous oligonucleotides; and
        a lysis buffer solution;
    incubating the lysis mixture for up to 30 minutes, thereby lysing the cell in the lysis mixture;
    preparing a neutralized mixture by adding a pH-neutralization solution to the lysis mixture following incubation; and
    performing isothermal whole genome amplification by:
        adding a polymerase, dNTPs, and a salt mixture to the neutralized mixture to prepare an amplification mixture, and
        incubating the amplification mixture under isothermal conditions to amplify the genomic DNA,
    wherein the concentration of red blood cells is about 2,500 to about 50,000 cells per microliter of amplification mixture.

2. The method of claim 1, wherein the lysis mixture comprises DNA from not more than one cell.

3. The method of claim 2, wherein the concentration of red blood cells is about 5,000 to about 50,000 cells per microliter of amplification mixture.

4. The method of claim 1, wherein prior to performing whole genome amplification, the method further comprises heating the neutralized mixture for less than 2 minutes to denature DNA in the neutralized mixture, and cooling the neutralized mixture.

5. The method of claim 4, wherein heating the neutralized mixture comprises heating the mixture at 80° C. to 95° C. for less than two minutes.

6. The method of claim 1, wherein the method does not further comprise heating the neutralized mixture prior to whole genome amplification.

7. A method of preparing genomic DNA from a cell for whole genome amplification, comprising:
    obtaining a sample comprising cells containing genomic DNA and red blood cells;
    aliquoting at least 300 subsamples of the sample, wherein the subsamples each contain an average of less than about one cell containing genomic DNA and red blood cells;
    adding to each subsample:
        oligonucleotides; and
        a lysis buffer solution;
    incubating the subsamples containing the oligonucleotides and lysis buffer solution for up to 30 minutes, thereby lysing the cells;
    preparing neutralized subsamples by adding a pH-neutralization solution and an amount of oligonucleotide primers sufficient for amplification of the genomic DNA to the lysed sub samples; and
    performing isothermal whole genome amplification by:
        adding a polymerase, dNTPs, and a salt mixture to a neutralized subsample to prepare an amplification mixture, and
        incubating the amplification mixture under isothermal conditions to amplify the genomic DNA,
    wherein the concentration of red blood cells is about 2,500 to about 50,000 cells per microliter of amplification mixture.

8. The method of claim 7, wherein the genomic DNA in the amplification mixture originates from a single cell.

9. The method of claim 8, wherein the incubation under isothermal conditions does not include a heat denaturation step.

10. The method of claim 9, further comprising dividing the product of the whole genome amplification into at least two aliquots.

11. The method of claim 10, further comprising performing a test on at least one of the aliquots to determine that the genomic DNA is from a fetal cell and/or to identify a genetic variation.

12. The method of claim 11, wherein whole genome amplification is performed on a plurality of amplification mixtures, wherein each of the plurality of amplification mixtures contains genomic DNA that originates from not more than one cell, the method further comprising:
    pooling aliquots from at least two amplification mixtures determined to contain genomic DNA from a fetal cell; and
    performing a second amplification on the pooled aliquots and/or performing a test on the pooled aliquots or second amplification product to identify a genetic variation.

13. The method of claim 10, further comprising performing a second amplification on at least one of the aliquots to provide a product of the second amplification.

14. The method of claim 13, further comprising:
    dividing the product of the second amplification into at least two subsamples; and
    performing a test on at least one of the subsamples from the second amplification to determine that the genomic DNA is from a fetal cell and/or to identify a genetic variation.

15. The method of claim 8, wherein the amplification mixture comprises $KPO_4$.

16. The method of claim 8, wherein at least a portion of the oligonucleotides or oligonucleotide primers are $SpC_3$—$N_9$ primers, wherein N is any nucleotide, and wherein $SpC_3$ is a three carbon molecule.

17. The method of claim 8, wherein the salt mixture comprises:
    Tris-HCl;
    NaCl or KCl;

MgCl$_2$ or MnCl$_2$;
and (NH$_4$)$_2$SO$_4$.

18. The method of claim 8, further comprising performing analysis of at least one characteristic selected from the group of a locus dropout rate, an allele dropout rate and fidelity value.

19. The method of claim 8, wherein whole genome amplification is performed on a plurality of amplification mixtures, wherein each of the plurality of amplification mixtures contains genomic DNA that originates from not more than one cell, the method further comprising:
   pooling the product of the whole genome amplification or a portion thereof, with the product of another whole genome amplification or portion thereof; and
   performing a second amplification on the pooled products.

20. The method of claim 8, wherein the concentration of red blood cells is about 5,000 to about 50,000 cells per microliter of amplification mixture.

21. The method of claim 7, wherein the sample is a sample from a pregnant woman comprising maternal cells and fetal cells, the method further comprising:

enriching the sample for fetal cells prior to aliquoting at least 300 subsamples of the sample;

dividing each of a plurality of whole genome amplification products into at least two aliquots;

performing a test on at least one of the aliquots to determine that the genomic DNA is from a fetal cell; and performing a test on an aliquot determined to contain genomic DNA from a fetal cell to identify a genetic variation in the genomic DNA.

22. The method of claim 7, wherein prior to performing whole genome amplification, the method further comprises heating the neutralized mixture for less than 2 minutes to denature DNA in the neutralized mixture, and cooling the neutralized mixture.

23. The method of claim 7, wherein the method does not further comprise heating the neutralized mixture prior to whole genome amplification.

* * * * *